United States Patent
Williams

(10) Patent No.: US 10,758,268 B2
(45) Date of Patent: Sep. 1, 2020

(54) SURGICAL INSTRUMENT INCLUDING SYSTEM FOR SENSING TISSUE PROPERTIES AND METHODS THEREOF

(71) Applicant: Covidien LP, Mansfield, MA (US)

(72) Inventor: Justin Williams, Southbury, CT (US)

(73) Assignee: COVIDIEN LP, Mansfield, MA (US)

( * ) Notice: Subject to any disclaimer, the term of this patent is extended or adjusted under 35 U.S.C. 154(b) by 162 days.

(21) Appl. No.: 16/140,664

(22) Filed: Sep. 25, 2018

(65) Prior Publication Data

US 2019/0175216 A1 Jun. 13, 2019

Related U.S. Application Data

(60) Provisional application No. 62/597,621, filed on Dec. 12, 2017.

(51) Int. Cl.
| | |
|---|---|
| *A61B 17/34* | (2006.01) |
| *A61B 17/11* | (2006.01) |
| *A61B 17/29* | (2006.01) |
| *A61B 5/00* | (2006.01) |
| A61B 17/00 | (2006.01) |
| A61B 90/00 | (2016.01) |

(52) U.S. Cl.
CPC ........ *A61B 17/3421* (2013.01); *A61B 5/6853* (2013.01); *A61B 17/11* (2013.01); *A61B 17/2909* (2013.01); *A61B 17/3462* (2013.01); *A61B 2017/0011* (2013.01); *A61B 2017/00022* (2013.01); *A61B 2017/00026* (2013.01); *A61B 2017/00367* (2013.01); *A61B 2017/00477* (2013.01); *A61B 2017/00557* (2013.01); *A61B 2017/00818* (2013.01); *A61B 2090/064* (2016.02)

(58) Field of Classification Search
CPC ......... A61B 5/6853; A61B 2017/00022–0011; A61B 2017/345; A61B 2017/22051; A61B 2017/20067; A61B 17/3421
See application file for complete search history.

(56) References Cited

U.S. PATENT DOCUMENTS

| | | | |
|---|---|---|---|
| 4,961,738 A | 10/1990 | Mackin | |
| 2009/0054803 A1 | 2/2009 | Saadat et al. | |
| 2014/0214025 A1* | 7/2014 | Worrell | A61B 18/1445 606/41 |
| 2015/0157320 A1 | 6/2015 | Zergiebel et al. | |
| 2016/0199092 A1 | 7/2016 | Patel et al. | |

(Continued)

OTHER PUBLICATIONS

Extended European Search Report corresponding to counterpart Patent Application EP 18211500.6 dated Apr. 1, 2019.

(Continued)

*Primary Examiner* — Thaddeus B Cox

(57) ABSTRACT

A surgical device for sensing a tissue property includes a handle, an outer cannula, an actuation assembly, and a sensing assembly. The handle is coupled to the outer cannula. The actuation assembly is slidably received by the outer cannula. The sensing assembly includes a fixed member, a shuttle, a sensor, and a bladder. The fixed member is disposed along a distal portion of the outer cannula. The shuttle is configured to slidably engage the fixed member. The sensor is disposed on the shuttle. The bladder is configured to be in fluid communication with the bladder pressurization device.

20 Claims, 6 Drawing Sheets

(56) References Cited

U.S. PATENT DOCUMENTS

| | | |
|---|---|---|
| 2016/0296234 A1 | 10/2016 | Richard et al. |
| 2016/0310134 A1 | 10/2016 | Contini et al. |
| 2017/0290603 A1 | 10/2017 | Piippo Svendsen et al. |
| 2018/0250002 A1 | 9/2018 | Eschbach |
| 2019/0000477 A1* | 1/2019 | Shelton, IV ..... A61B 17/07207 |

OTHER PUBLICATIONS

U.S. Appl. No. 16/140,664, filed Sep. 25, 2018.
U.S. Appl. No. 62/661,821, filed Apr. 24, 2018.
U.S. Appl. No. 62/661,242, filed Apr. 25, 2018.

* cited by examiner

SURGICAL INSTRUMENT INCLUDING SYSTEM FOR SENSING TISSUE PROPERTIES AND METHODS THEREOF

CROSS-REFERENCE TO RELATED APPLICATION

This application claims the benefit of and priority to U.S. Provisional Patent Application No. 62/597,621 filed Dec. 12, 2017, the entire disclosure of which is incorporated by reference herein.

BACKGROUND

Technical Field

The present disclosure relates generally to surgical instruments and, more particularly, to systems and methods for measuring one or more tissue properties during a surgical procedure.

Related Art

During surgical procedures medical professionals or clinicians may find it desirable to determine one or more tissue properties prior to acting upon the tissue. For example, during colorectal surgeries which require anastomosis, the clinician visually inspects the tissue of the colon to be resected. Typically, during inspection, the clinician visually observes the colon and determines which portion or portions of the colon are diseased. The clinician then identifies which diseased portions of the colon will be removed. Observation may be performed via one or more imaging devices positioned within the colon or proximate to the colon. Various other surgical procedures require similar visual inspection of tissue to determine which portions of tissue are to be removed.

Depending on the procedure and the tissue being examined, the clinician may not identify all areas of concern due to the limited visibility of the clinician. For example, referring again to anastomotic procedures, the colon may include an abnormal growth which may not be easily visualized from an inspection of the exterior of the colon. As such, the clinician may need to inspect the interior of the tissue to be resected as well. Inspection of the interior of the colon may require additional clinicians to assist in imaging the interior of the colon. Additionally, care must be taken when aligning the interior and exterior views during the imaging process.

As such, improved systems and methods for evaluating tissue properties during a surgical procedure are desirable.

SUMMARY

Existing challenges associated with the foregoing, as well as other challenges, are overcome by methods for identifying one or more properties of target tissue, and also by systems, and apparatuses that operate in accordance with the methods.

In accordance with an aspect of the present disclosure, a surgical device for sensing a tissue property includes a handle, an outer cannula, an actuation assembly slidably received by the outer cannula, and a sensing assembly. The handle is coupled to the outer cannula. The actuation assembly is slidably received by the outer cannula. The sensing assembly includes a fixed member, a shuttle, a sensor, and a bladder. The fixed member is disposed along a distal portion of the outer cannula. The shuttle is configured to slidably engage the fixed member. The sensor is disposed on the shuttle. The bladder is configured to be in fluid communication with bladder pressurization devices.

In aspects, the surgical device further includes a fluid conduit coupled to the bladder. The fluid conduit may be configured to be coupled to a bladder pressurization device. The actuation assembly may include an inner cannula. The inner cannula may be configured to be slidably received by the outer cannula. The handle, the outer cannula, and the inner cannula may include corresponding openings configured to permit passage of a fluid conduit therethrough.

According to aspects, the shuttle may further include an arm including at least one tooth disposed along the arm of the shuttle. The fixed member may further include an arm including at least one tooth configured to selectively engage the at least one tooth of the arm of the shuttle. The bladder may be configured to selectively engage the arm of the fixed member. The arm of the fixed member may be biased toward the center of the outer cannula.

In aspects, the surgical device may include a first spring disposed along a proximal portion of an inner cannula. The first spring may be configured to apply a proximal force to a knob coupled to a proximal portion of the inner cannula. The first spring may be configured to apply a distal force to a pin coupled to the handle. The surgical device may include a second spring disposed between the fixed member and the shuttle. The second spring may be configured to engage the sensing assembly. The second spring may be configured to apply a distal force to the fixed member. The second spring may be configured to apply a proximal force to the shuttle.

According to aspects, the first spring and the second spring may be configured to maintain the surgical device in a closed position. The actuation assembly may be configured to receive a distal force sufficient to overcome the force applied by the first spring and the second spring to cause the actuation assembly to engage the sensing assembly. The actuation assembly may be configured to apply force to the target tissue when the sensing assembly is positioned about the target tissue while the proximal force is applied by the first spring or the second spring to cause the sensing assembly to move proximally toward the closed position.

In aspects, when the bladder of the surgical device is expanded, the bladder may be configured to apply a force to the target tissue to cause the target tissue to engage the sensor. The bladder may be configured to apply sufficient force to occlude blood flow through the target tissue. The sensor may be selected from the group consisting of piezoresistive force sensors, optical sensors, and impedance sensors.

BRIEF DESCRIPTION OF THE DRAWINGS

The accompanying drawings, which are incorporated in and constitute a part of the specification, illustrate embodiments of the present tissue sensing devices and methods and, together with a general description of the disclosure given above, and the detailed description of the embodiment(s) given below, serve to explain the principles of the disclosure.

DETAILED DESCRIPTION

Figure 1:
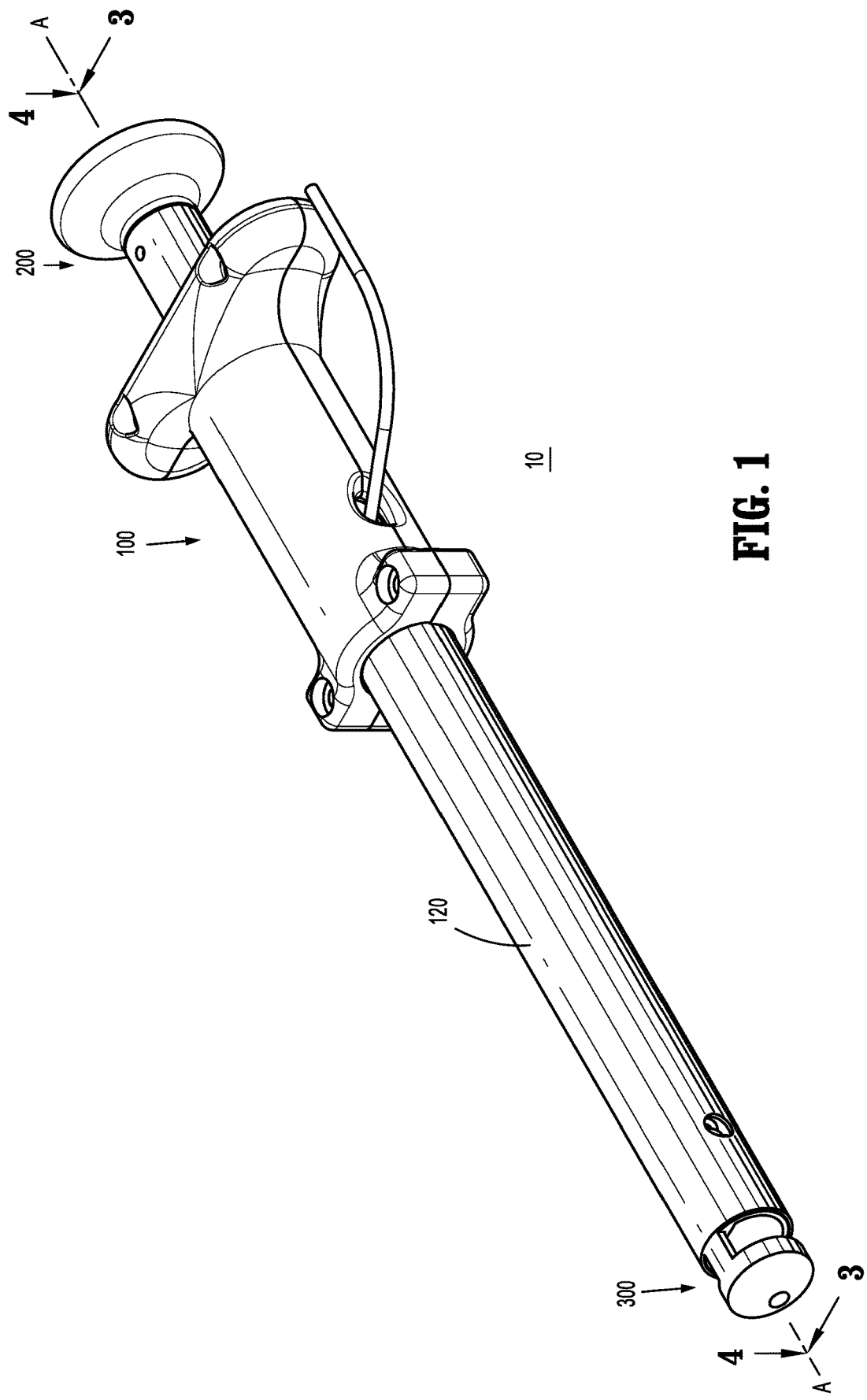
FIG. 1 is a perspective view of a tissue property sensing device in accordance with an embodiment of the present disclosure.

Embodiments of the present tissue sensing devices and methods are described in detail with reference to the drawings, in which like reference numerals designate identical or corresponding elements in each of the several views.

Reference will be made to the terms described herein while describing the principles outlined by the present disclosure. As used herein, the term "clinician" refers to a doctor, nurse, or other care provider and may include support personnel. The term "distal" refers to structure that is, in use, positioned farther from the clinician, while the term "proximal" refers to structure that is closer to the clinician. Further, directional terms such as front, rear, upper, lower, top, bottom, distal, proximal, and the like are used to assist in understanding the description and are not intended to limit the present disclosure. The term "surgical field" refers to the space in which the surgical procedure is performed, and the term "surgical cavity" refers to a cavity at least partially surrounded by tissue.

Tissue property sensing devices in accordance with illustrative embodiments of the present disclosure include a handle coupled to an outer cannula, an actuation assembly, and a sensing assembly. In use, the clinician applies distal force to a knob of the tissue property sensing device to advance a shuttle of the sensing assembly distally relative to a distal portion of the tissue property sensing device. After the shuttle is advanced distally relative to the outer cannula the tissue property sensing device is in an "OPEN" configuration, and the target tissue is positioned with a cavity formed by the shuttle. Once the clinician is satisfied with the placement of the target tissue within the cavity, the clinician releases the distal force applied to the knob while maintaining a grasp on the tissue property sensing device. As force applied to the knob is applied or reduced, the tissue property sensing device and, more particularly, the sensing assembly is maintained in fixed relation to the target tissue while the target tissue is pinned or clamped between components of the sensing assembly. When the target tissue is clamped, one or more properties are measured by sensors associated with the sensing assembly. The sensing assembly may be further coupled to a bladder pressurization device (not shown). To increase the force applied to the target tissue, the bladder pressurization device may be engaged, thereby causing gas or fluid (referred to herein as "fluid" for clarity) to be selectively maintained in the bladder.

Referring initially to FIG. 1, one embodiment of a tissue property sensing device is shown and generally referred to as a surgical device 10. The surgical device 10 defines a longitudinal axis A-A and includes a handle 100, an actuation assembly 200, and a sensing assembly 300. The handle 100 includes an outer cannula 120 extending through a bore defined by the handle 100, wherein the bore extends along the longitudinal axis A-A. The outer cannula 120 is configured to slidably receive the actuation assembly 200 therein, the actuation assembly 200 moving proximally and distally relative to the outer cannula 120.

With reference to FIGS. 1-4, the actuation assembly 200 is configured to move proximally and distally along the longitudinal axis A-A relative to the outer cannula 120. The actuation assembly 200 includes an inner cannula 220 which is slidably received along an interior surface defined by the outer cannula 120. The inner cannula 220 defines a proximal portion 220a and a distal portion 220b. The proximal portion 220a of the inner cannula 220 is configured to couple to a knob 202. The knob 202 includes a proximal engagement surface 204 which is indented distally to facilitate engagement of the knob 202 by the thumb of a clinician. Similarly, the outer surface of the knob 202 has a frustoconical shape configured to receive proximal forces exerted by clinicians during surgical procedures. The knob 202 may receive proximal or distal forces, and in response to receiving the respective force, cause the inner cannula 220 to move relative to the outer cannula 120 between a proximal-most position (FIG. 5C) and distal-most position (FIG. 5A). Movement of the inner cannula 212 between proximal and distal positions causes the inner cannula 212 to selectively engage the sensing assembly 300.

The sensing assembly 300 is configured to, when engaged by the inner cannula 220, apply or reduce force exerted on target tissue (not shown) when the target tissue is located along an interior portion of the sensing assembly 300. As force is applied or relieved from the sensing assembly 300, the target tissue may be compressed or decompressed, thereby facilitating selective engagement of the tissue with a sensor "S" (FIG. 3) associated with the sensing assembly 300. Additionally, or alternatively, fluid may be introduced to the surgical device 10, such as gases or liquids, which cause a bladder "B" (see FIGS. 2-5C) of the surgical device 10 to engage the target tissue.

Figure 2:
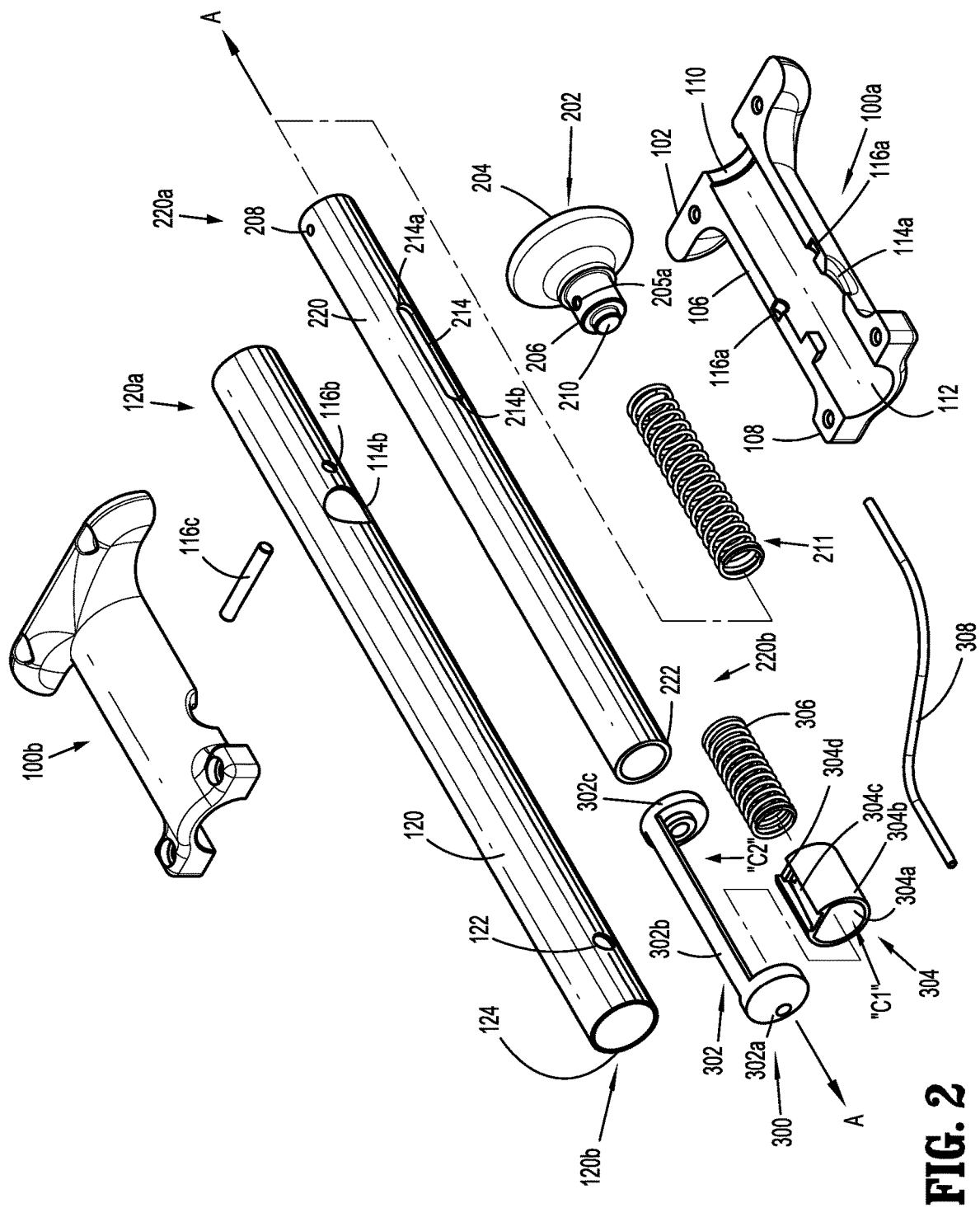
FIG. 2 is an exploded perspective view of the tissue property sensing device of FIG. 1.

Referring to FIG. 2, as illustrated by the disassembled surgical device 10 of FIG. 1, the handle 100 includes a first half portion 100a and a second half portion 100b. The first and second half portions 100a, 100b are in mirrored relation and are configured to be coupled to and about a proximal portion of the outer cannula 120. For purposes of clarity the handle 100 will be described when the first half portion 100a and second half portion 100b are coupled. The handle 100 includes a proximal flange 102 and a distal flange 108. The proximal flange 102 is located proximal to a body portion 106 of the handle 100. The distal flange 108 is located distal to the body portion 106. The body portion 106 is configured to be gripped by the hand of a clinician (not shown), with the proximal flange 102 and the distal flange 108 further configured to receive force exerted by the clinician and provide support as the clinician grasps the surgical device 10.

The handle 100 is configured to couple about a proximal portion of the outer cannula 120. When the handle 100 is coupled about the outer cannula 120, an inner surface 112 of the handle 100 is positioned adjacent to the proximal portion of an outer surface defined by the outer cannula 120. Corresponding fastening openings or bores 104 disposed in fixed relation along the handle 100 may receive fasteners therein (not shown) when the handle 100 is coupled to the proximal portion of the outer cannula 120, thereby fixably coupling the handle 100 to the outer cannula 120.

The handle 100 includes a pair of opposing lateral recesses 116a which are configured to receive a pin 116c therein. The pin 116c is additionally received by openings 116b of the outer cannula 120 therethrough. As a result, when the surgical device 10 is engaged by a clinician, the handle 100 remains in a fixed position relative to the outer cannula 120.

The handle 100 further includes an opening 114a which align with an opening 114b of the outer cannula 120. The openings 114a, 114b permits passage of a fluid conduit 308 through the handle 100 and the outer cannula 120, respectively.

The outer cannula 120 is configured to slidably receive an inner cannula 220 of the actuation assembly 200 therein. The inner cannula 220 includes a base connection opening 208, a pair of windows 214, and a distal engagement portion 222. The knob 202 includes a distal member 206 configured to be inserted into a proximal portion 220a of the inner cannula 220. The distal member 206 includes an opening 205a defining a bore extending transverse relative to axis A-A. When the knob 202 is inserted into the proximal portion 220a of the inner cannula 220, and the opening 205a is aligned with the base connecting opening 208, a pin (not shown) may be inserted therethrough to maintain the knob 202 in fixed relation to the inner cannula 220.

The windows 214 extend longitudinally parallel to the A-A axis, and are configured to receive one or more fluid conduits 308 therethrough. The windows 214 includes a proximal portion 214a and a distal portion 214b configured to limit motion of the inner cannula 220 relative to the outer cannula 120. More particularly, as the inner cannula 220 is translated proximally or distally relative to the outer cannula 120 the pin 116c, extending through the windows 214, engages the proximal portion 214a or the distal portion 214b of the windows 214. As a result, when the pin 116c engages the proximal portion 214a or the distal portion 214b of the windows 214, the inner cannula 212 reaches a limit and is prevented from translating further in the direction which the inner cannula 212 was traveling. It should be noted that the windows 214 may not be in mirrored relation so as to prevent engagement or crimping of fluid conduits 308 extending through the window 214 by the outer cannula 120 or inner cannula 220.

The handle 100 further includes a spring 211 positioned between a nub 210 extending distally from the knob 202 and the pin 116c. When positioned between the knob 202 and the pin 116, the spring 211 is configured to transmit proximal and distal forces against both the nub 210 and the pin 116c, respectively. As the spring 211 transmits proximal and distal forces to the nub 210 and the pin 116c, the transmitted force causes the knob 202 to be biased to a proximal position relative to the surgical device 10 by default. When a distal force is applied to the knob 202, the knob 202 is translated distally relative to the spring 211. In response to the application of distal force to the knob 202, the spring 211 is configured to compress, permitting slidable translation of the inner cannula 220 along a portion of the outer cannula 120.

The windows 214 may be configured to limit motion of the inner cannula 220 relative to the outer cannula 120. More particularly, as the inner cannula 220 translates relative to the outer cannula 120, the proximal portion 214a and the distal portion 214b of the window 214 may be positioned along the inner cannula 220 such that the proximal and distal portions 214a, 214b of the window 214 contact the pin 116c once the inner cannula 220 is translated to a proximal-most or distal-most position. Depending on the placement of the windows 214 along the inner cannula, one window 214 may prevent the crimping or obstruction of the flow of fluid through the fluid conduit 308 by limiting translation of the window 214 which receives the fluid conduit 308 therethrough. Additionally, the windows 214 are configured to limit rotation of the inner cannula 220 relative to the outer cannula 120.

Figure 3:
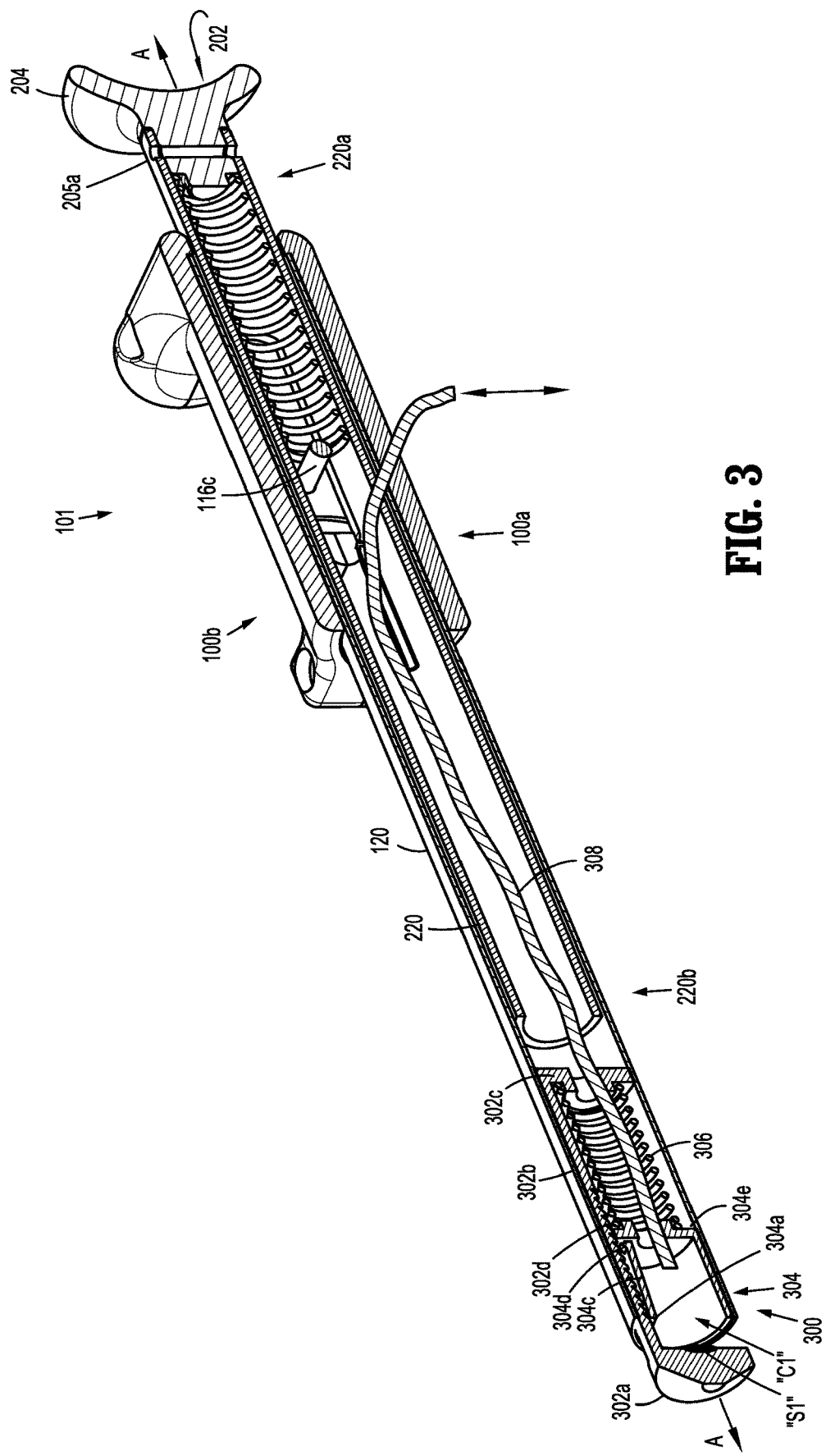
FIG. 3 is a perspective view of the tissue property sensing device of FIG. 1, taken along section line 3-3 of FIG. 1.
Figure 4:
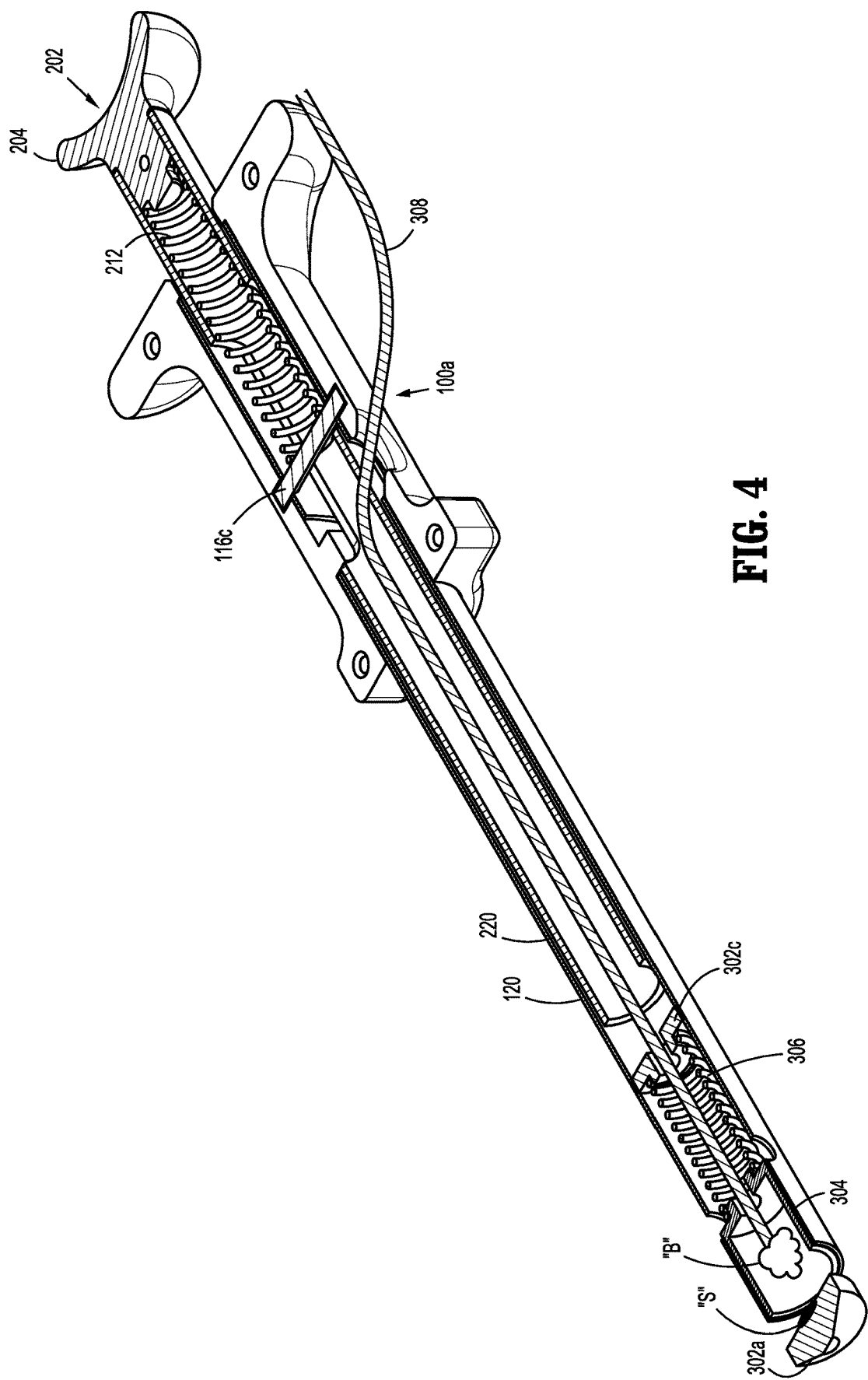
FIG. 4 is a perspective view of the tissue property sensing device of FIG. 1, taken along section line 4-4.
Figure 5A:
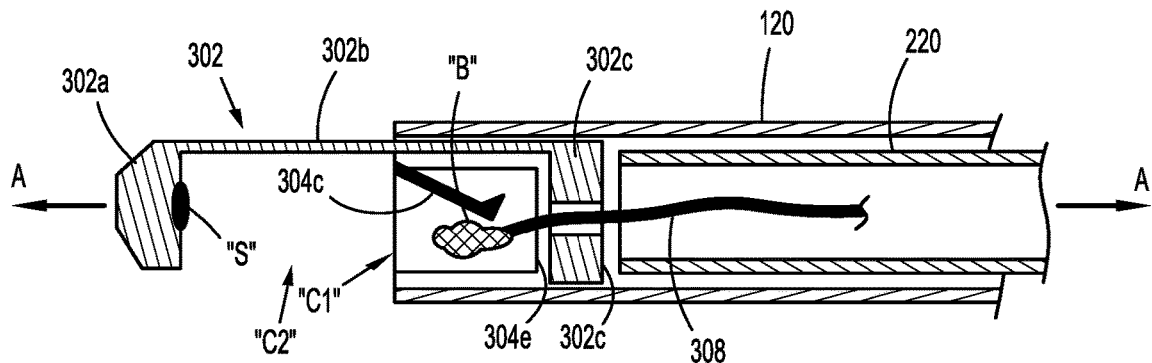
FIG. 5A is a side plan view of the tissue property sensing device of FIG. 1 in an open configuration, taken along 3-3.
Figure 5B:
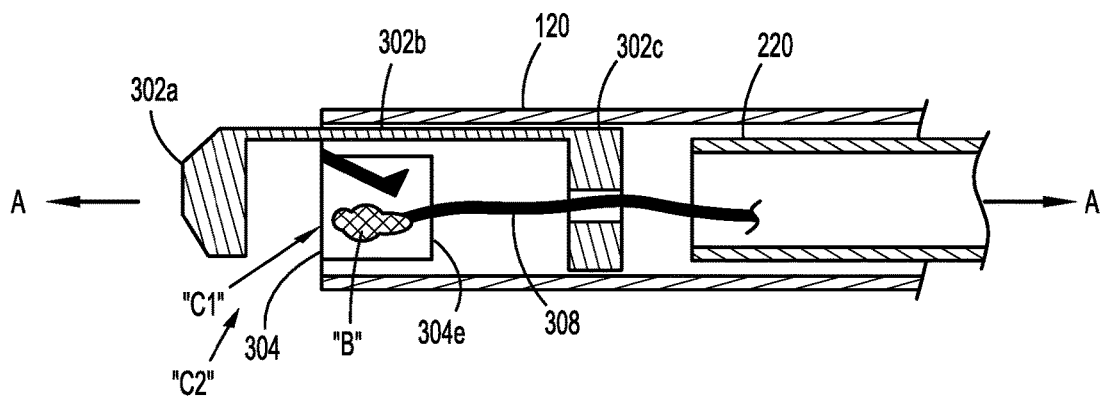
FIG. 5B is a side plan view of the tissue property sensing device of FIG. 1 in a closed configuration, with a bladder deflated, taken along 3-3.
Figure 5C:
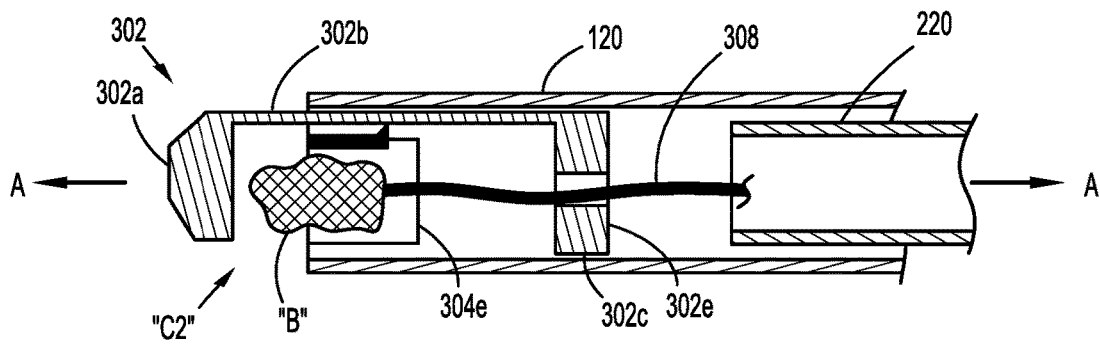
FIG. 5C is a side plan view of the tissue property sensing device of FIG. 1 in a closed configuration, with the bladder inflated, taken along 3-3.

Referring now to FIGS. 1-4, and specifically FIGS. 3 and 4, the sensing assembly 300 is shown coupled to a distal portion of the outer cannula 120. The sensing assembly 300 is configured to be engaged by the inner cannula 220 and by a bladder pressurization device (not shown). The sensing assembly 300 includes a fixed member 304 coupled (fixed) internally along the proximal portion 120a of the outer cannula 120. The fixed member 304 includes an outward-biased arm or biasing arm 304c and a spring receiving member 304e. The fixed member 304 further defines a recess or opening "C1" located within the distal portion 120a of the outer cannula 120. The inner surface 304a, defined by the fixed member 304, is configured to slidably receive a shuttle arm 302b of a shuttle 302 therethrough. The biasing arm 304c further defines one or more teeth 304d configured to engage teeth 302d disposed along the shuttle arm 302b. Absent the application of radial force from the bladder "B", the biasing arm 304c is configured to be biased toward the central portion of the fixed member 304.

The sensing assembly 300 further includes a shuttle 302 having a shuttle head or compression head 302a, the shuttle arm 302b, and a shuttle base 302c. The compression head 302a and shuttle base 302c are coupled proximally and distally to the shuttle arm 302b, respectively. The shuttle arm 302b further defines a set of teeth which are configured to be engaged by the one or more teeth of the shuttle arm 302b. The compression head 320a includes a sensor "S" disposed on an inner proximally facing surface of the compression head 320.

The sensing assembly 300 further includes a spring 306 is positioned between the fixed member 304 and the shuttle base 302c. The spring 306 is configured to apply proximal and distal forces to the shuttle base 302c and the spring receiving member 304e, respectively. As a result, absent engagement of the sensing assembly 300 by the inner cannula 220 or the bladder pressurization device (not shown), the sensing assembly 300 is configured to remain in a "CLOSED" position by default. The sensing assembly 300 is maintained in the "CLOSED" position by the spring 306 which exerts proximal and distal forces to the shuttle base 302c and the spring receiving member 304e. To transition the sensing assembly 300 from the "CLOSED" position (FIG. 5C) toward the "OPEN" position (FIG. 5A), force is applied to the shuttle 302 by the distal engagement portion 222 of the inner cannula 220. When sufficient force is exerted on the knob 202 by clinicians to overcome force exerted on the shuttle 302 by the spring 306, the shuttle 302 advances distally relative to the outer cannula 120, thereby transitioning the sensing assembly 300 to the "OPEN" position.

The sensing assembly 300 also includes a bladder "B" positioned in a cavity "C1" defined by the fixed member 304. The bladder "B" is coupled to the fluid conduit 308. As noted earlier, the fluid conduit 308 is in fluid communication with a bladder pressurization device (not shown), and operably couples the bladder "B" to the bladder pressurization device. The bladder "B", when in a distended or expanded state, is configured to apply force outward toward an inner surface 304a defined by the fixed member 304, and the compression head 302a. Alternatively, when in a deflated state, the bladder "B" is configured to reduce or eliminate the outward force applied during expansion of the bladder. More particularly, when target tissue is positioned between the bladder "B" and the compression head 302a, as the bladder "B" is expanded, outward force is directed toward the compression head 302a and received at least in part by the target tissue positioned therebetween. It is contemplated that the bladder "B" may be attached to the fixed member 304 via an adhesive, a hook and loop fastener, a suture, or the like. It is further contemplated that the bladder "B" may be detachably coupled to the fixed member 304.

When the bladder "B" is expanded, the bladder "B" also applies force, radially outward, toward the biasing arm 304c of the fixed member 304. Once sufficient outward force is applied by the bladder "B" to the biasing arm 304c, the teeth 302d of the shuttle arm 302b engage the teeth 304d of the biasing arm 304c. Engagement of the shuttle arm 302b by the teeth 304d of the biasing arm 304c limits distal motion of the shuttle 302, thereby preventing the shuttle 302 from advancing distally when toward the distal-most or "OPEN" position.

As noted earlier, the proximal surface of the compression head 302a of the shuttle 302 includes at least one sensor "S" disposed thereon. The sensor "S" may include one or more sensors which may be fixed to the proximal surface of the compression head 302a via any suitable method including, but not limited to, fixation with an adhesive, one or more fasteners (not shown), clips or other similar structures disposed along the compression head 302a. The sensor "S" may include one or more piezoresistive force sensors, optical sensors, or impedance sensors.

The sensor "S" may be in wired or in wireless communication with a computing device 400 (FIG. 6) coupled or otherwise in electrical communication with a display device (not shown). The sensor "S" is configured to transmit sensor signals therefrom and, more particularly, as the sensor "S" is engaged by the tissue during a sensing procedure, the sensor "S" is configured to transmit sensor signals indicative of blood profusion, tissue health, blood force, blood profusion, tissue impedance, tissue profusion, etc.

The handle 100, outer cannula 120, inner cannula 220, actuation assembly 200 and sensing assembly 300 may be manufactured using materials known in the art, such as plastics, polymers, biocompatible materials, metals, and other similar materials known in the art. The fluid conduit 308 may be made of plastics, rubbers, or other similar materials capable of delivering pressurized fluids to the bladder "B". The bladder may be fabricated from a biocompatible material such as natural or synthetic elastomers, natural or synthetic rubbers, silicone materials, and/or compliant elastomers.

Reference will now be made to operation of the surgical device 10 during a surgical procedure performed by a clinician. When the clinician determines that it would be desirable to measure one or more tissue properties during a surgical procedure, the clinician may insert the distal portion of the surgical device 10 into a surgical cavity of a patient. The surgical device 10, and more particularly the sensing assembly 300, may be in the "CLOSED" position due to force applied by the springs 211, 306 so as to prevent inadvertent engagement of tissue by the sensing assembly 300. The bladder "B" may additionally be distended while the surgical device 10 is guided toward the target tissue to prevent inadvertent distal motion of the shuttle 302 relative to the surgical device 10. Once inserted, the clinician may guide the distal portion of the surgical device 10 toward target tissue.

After identifying the target tissue, while the bladder "B" is deflated, the clinician may grasp the handle 100 and apply distal force to the knob 202 relative to the handle 100. As distal force is applied to the knob 202, the clinician applies an approximately equal amount of counter force to the handle 100, so as to maintain the handle 100 in fixed relation to the tissue. While distal force is applied to the knob 202, the distal portion 220b of the inner cannula 220 applies force distally to the shuttle base 302c. In turn, the shuttle base 302c transfers the distal force to both the shuttle arm 302b and the compression head 302a, thereby causing the compression head 302a to advance distally toward an "OPEN" position. Concomitantly, the spring 306 is compressed between the distal portion 220b of the inner cannula 220 and the shuttle base 302c of the shuttle 302.

Once in the "OPEN" position, the sensing assembly 300 may be positioned around the target tissue by positioning the target tissue within a cavity "C2" of the shuttle 302. More particularly, the target tissue is positioned between the compression head 302a and the distal portion 120b of the outer cannula 120. Once the target tissue is situated such that the majority of the target tissue is positioned central to the longitudinal axis A-A, the clinician may reduce or release the distal force exerted on the knob 202. In response, the shuttle 302, and more specifically the compression head 302a, is advanced proximally toward the fixed member 304 and engages the target tissue, e.g., clamps the target tissue.

The bladder "B" may be partially or fully expanded prior to release of distal force by the clinician on the knob 202. As the target tissue is compressed between the compression head 302a and the bladder "B", or the distal portion 120b of the outer cannula 120, the target tissue is fixed in position relative to the surgical device 10. The clinician may then engage the bladder pressurization device, thereby causing fluid force to build up in the bladder "B". The increase in fluid force in the bladder "B" causes the target tissue to be further compressed between the bladder "B" and the compression head 302a. Additionally, the increase in force fixes the compression head 302a relative to the outer cannula 120 as the bladder "B" presses the biasing arm 304c into engagement with the teeth 304d of the shuttle arm 304b. In embodiments, a computing device 400 (FIG. 6) may transmit control signals to cause the bladder pressurization device to inflate or deflate the bladder "B". More particularly, the bladder pressurization device may receive signals to inflate or deflate Once the desired amount of compression is exerted on the target tissue, the sensor "S" may transmit sensor signals to the computing device 400 (FIG. 6) to be displayed on a display (not shown). The display may display data indicative of the sensor measurements at a specified time, at periodic intervals, or continuously. Once the desired sensor measurements are noted by the clinician, the clinician may cause the bladder pressurization device to reduce the force applied by the bladder "B". As force is released, bladder "B" permits the teeth 304d located on the biasing arm 304c of the fixed member 304 to disengage the teeth 302e of the shuttle arm 302b, which in turn permits the clinician to apply distal force to the knob 202 to free the target tissue from the surgical device 10. As the clinician applies distal force, the compression head 302a extends distally. Once the target tissue is free from the surgical device 10, the clinician may cease applying distal force to the knob 202, and allow the surgical device 10, and more particularly the sensing assembly 300, to return to the "CLOSED" position.

Figure 6:
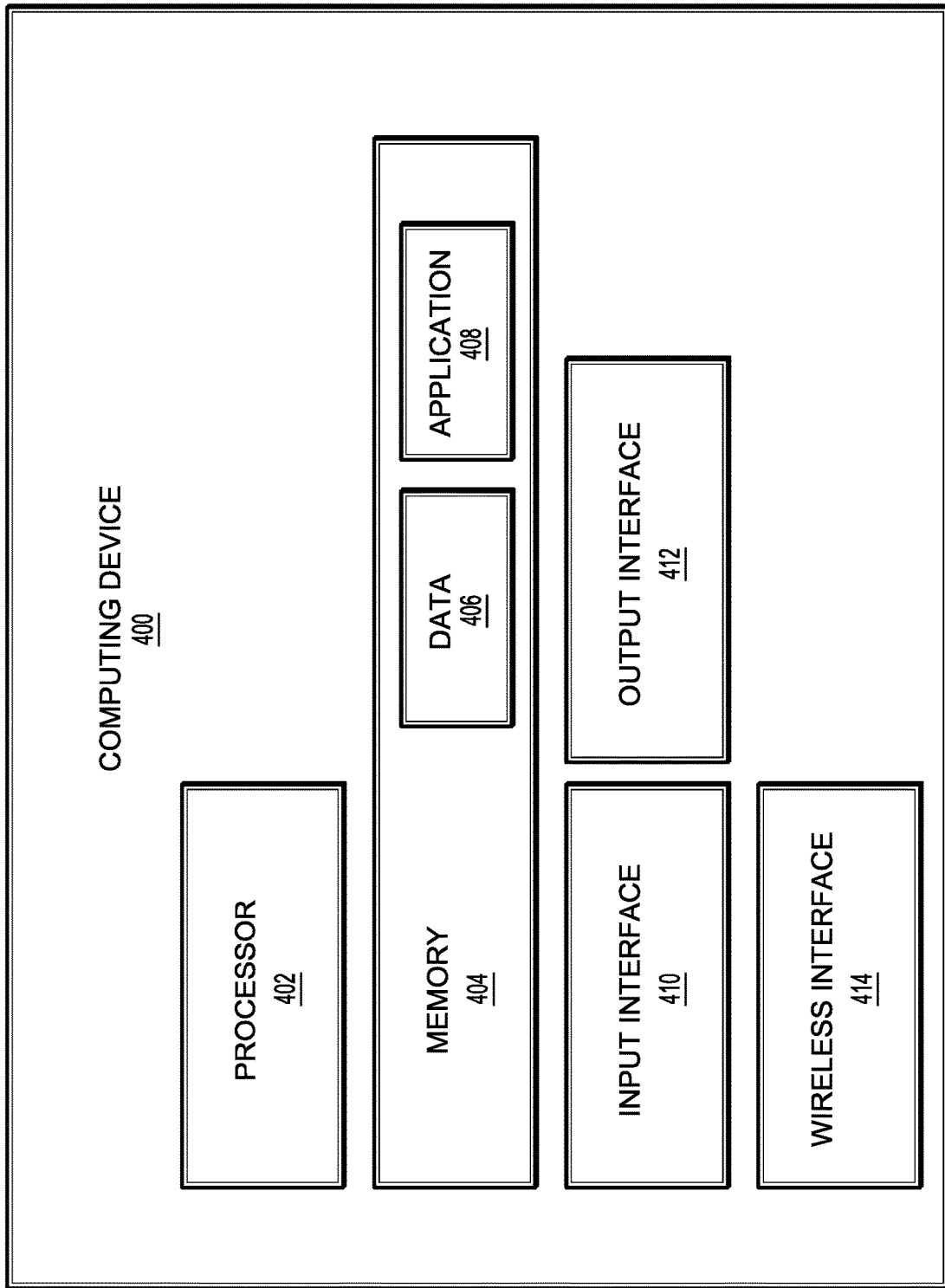
FIG. 6 is a schematic block diagram of a computing device 400 that may be employed according to various embodiments of this disclosure.

Referring now to FIG. 6, illustrated is a schematic block diagram of a computing device 400 that may be employed according to various embodiments of the present disclosure. Though not explicitly shown in corresponding figures of the present application, the computing device 400, or one or more components thereof, may represent one or more components (e.g., a controller, input interface, output interface, and the like) of the surgical device 10. The computing device 400 may include one or more processors 402, memories 404, input interfaces 410, output interfaces 412, wireless interfaces 414, or any desired subset of components thereof. The memory 404 includes non-transitory computer-readable storage media for storing data and/or software which include instructions that may be executed by the one or more processors 402. When executed, the instructions may cause the processor 402 to control operation of the computing device 400, e.g., reception and transmission of sensor signals transmitted and received during operation of the at least one sensor "S" located along the surgical device 10 (FIG. 3). In embodiments, the memory 404 may include one or more solid-state storage devices such as flash memory chips. Additionally, or alternatively, the memory 404 may include one or more mass storage devices in communication with the processor 402 through a mass storage controller and a communications bus (not shown). Although the description of computer readable media described in this disclosure refers to a solid-state storage device, it will be appreciated by one of ordinary skill that computer-readable media may include any available media that can be accessed by a processor 402. More particularly, computer readable storage media may include non-transitory, volatile, non-volatile, removable, non-removable media, and the like, implemented in any method of technology for storage of information such as computer readable instructions, data structures, program modules, or other suitable data access and management systems. Examples of computer-readable storage media include RAM, ROM, EPROM, EEPROM, flash memory, or other known solid state memory technology, CD-ROM, DVD, Blu-Ray, or other such optical storage, magnetic cassettes, magnetic tape, magnetic disk storage or other magnetic storage devices, or any other medium which may be used to store information and which can be accessed by computing device 400.

In embodiments, the memory 404 stores data 406 and/or one or more applications 408. Such applications 408 may include instructions which are executed on the one or more processors 402 of the computing device 400. The applications 408 may include instructions which cause an input interface 410 and/or an output interface 412 to receive and transmit sensor signals, respectively, to and from the surgical device 10. More particularly, as the at least one sensor "S" (see FIG. 3) senses one or more of the tissue properties discussed above, the at least one sensor "S" may, in response, transmit signals indicative of the measurements to the input interface 410, or by an external computing device 400. Once received by the input interface 410, the signals transmitted by the one or more sensors "S" may be stored in the at least one memory 404 of the computing device 400. Additionally, or alternatively, the computing device 400 may transmit the signals for analysis and/or display via the output interface 412. For example, the output interface 412 may transmit the sensor signals to a display device (not shown) either disposed on the surgical device 10 or located remotely relative to the surgical device 10. The memory 404 may further transmit and/or receive data via a wireless interface 414 via one or more wireless configurations, e.g., radio frequency, optical, Wi-Fi, Bluetooth (an open wireless protocol for exchanging data over short distances, using short length radio waves, from fixed and mobile devices, creating personal area networks (PANs), ZigBee® (a specification for a suite of high level communication protocols using small, low-power digital radios based on the IEEE 802.15.4-2003 standard for wireless personal area networks (WPANs)). Although depicted as a separate component, the wireless interface 414 may be integrated into the input interface 410 and/or the output interface 412.

Although the illustrative embodiments of the present disclosure have been described herein, it is understood that the disclosure is not limited to those precise embodiments, and that various other changes and modifications may be affected therein by one skilled in the art without departing from the scope or spirit of the present disclosure. All such changes and modifications are intended to be included within the scope of the present disclosure.

What is claimed is:

1. A surgical device for sensing a tissue property, the surgical device comprising:
a handle;
an outer cannula coupled to the handle;
an actuator slidably received by the outer cannula; and
a sensing assembly including:
a biasing arm disposed along a distal portion of the outer cannula;
a shuttle configured to slidably engage the biasing arm;
a sensor disposed on the shuttle; and
a bladder,
wherein the bladder is configured to be in fluid communication with a bladder pressurizer,
wherein the biasing arm is biased toward a center of the outer cannula, and
wherein the biasing arm is urged away from the center of the outer cannula when the bladder is inflated.

2. The surgical device of claim 1, further including a fluid conduit coupled to the bladder, the fluid conduit configured to be coupled to the bladder pressurizer.

3. The surgical device of claim 2, wherein the actuator includes an inner cannula configured to be slidably received by the outer cannula.

4. The surgical device of claim 3, wherein the handle, the outer cannula, and the inner cannula include corresponding openings configured to permit passage of a fluid conduit therethrough.

5. The surgical device of claim 1,
wherein the shuttle further includes an arm including at least one tooth disposed along the arm of the shuttle, and
wherein the biasing arm further includes at least one tooth configured to selectively engage the at least one tooth of the arm of the shuttle.

6. The surgical device of claim 5, wherein the bladder is configured to selectively engage the biasing arm.

7. The surgical device of claim 5, further comprising a first spring disposed along a proximal portion of an inner cannula, wherein the first spring is configured to apply a proximal force to a knob coupled to a proximal portion of the inner cannula and a distal force to a pin coupled to the handle.

8. The surgical device of claim 7, further comprising a second spring disposed between the biasing arm and the shuttle, the second spring configured to engage the sensing assembly.

9. The surgical device of claim 8, wherein the second spring is configured to apply a distal force to the biasing arm and a proximal force to the shuttle.

10. The surgical device of claim 9, wherein the first spring and the second spring are configured to maintain the surgical device in a closed position.

11. The surgical device of claim 10, wherein the actuator is configured to receive a distal force sufficient to overcome forces applied by the first spring and the second spring to cause the actuator to engage the sensing assembly.

12. The surgical device of claim 11, wherein the actuator is configured to apply force to target tissue when the sensing assembly is positioned about the target tissue while the proximal force is applied by the first spring or the second spring to cause the sensing assembly to move proximally toward the closed position.

13. The surgical device of claim 12, wherein when the bladder is expanded, the bladder is configured to apply a force to the target tissue to cause the target tissue to engage the sensor.

14. The surgical device of claim 13, wherein the bladder is configured to apply sufficient force to occlude blood flow through the target tissue.

15. The surgical device of claim 1, wherein the sensor is selected from the group consisting of piezoresistive force sensors, optical sensors, and impedance sensors.

16. A surgical device for sensing a tissue property, the surgical device comprising:
   an outer cannula;
   an actuator slidably received by the outer cannula; and
   a sensing assembly including:
      a biasing arm disposed along a distal portion of the outer cannula;
      a shuttle configured to slidably engage the biasing arm;
      a sensor disposed on the shuttle; and
      an inflatable bladder,
   wherein the biasing arm is biased toward a center of the outer cannula, and
   wherein the biasing arm is urged away from the center of the outer cannula when the inflatable bladder is inflated.

17. The surgical device of claim 16, wherein:
   the shuttle further includes an arm including at least one tooth disposed along the arm of the shuttle, and
   the biasing arm further includes at least one tooth configured to selectively engage the at least one tooth of the arm of the shuttle.

18. The surgical device of claim 17, wherein the inflatable bladder is configured to selectively engage the biasing arm.

19. The surgical device of claim 17, further comprising a first spring disposed along a proximal portion of an inner cannula, wherein the first spring is configured to apply a proximal force to a knob coupled to a proximal portion of the inner cannula.

20. The surgical device of claim 19, further comprising a second spring disposed between the biasing arm and the shuttle, the second spring configured to engage the sensing assembly.

* * * * *